United States Patent
Lepage (10) Patent No.: US 7,553,353 B2
(45) Date of Patent: Jun. 30, 2009

(54) SYSTEM FOR TREATING CONTAMINATED GAS

(76) Inventor: Jean-Pierre Lepage, 3425 Anatole Carignan, Lachine (Québec) (CA) H8T 3M9

( * ) Notice: Subject to any disclaimer, the term of this patent is extended or adjusted under 35 U.S.C. 154(b) by 206 days.

(21) Appl. No.: 10/588,795

(22) PCT Filed: Feb. 10, 2005

(86) PCT No.: PCT/CA2005/000167
§ 371 (c)(1),
(2), (4) Date: Aug. 21, 2007

(87) PCT Pub. No.: WO2005/077523
PCT Pub. Date: Aug. 25, 2005

(65) Prior Publication Data
US 2008/0035472 A1     Feb. 14, 2008

(30) Foreign Application Priority Data
Feb. 11, 2004   (CA)   .................................. 2457456

(51) Int. Cl.
*B03C 3/016*   (2006.01)
(52) U.S. Cl. .............. 96/3; 96/19; 96/22; 96/24; 96/68; 96/80; 96/97; 96/99; 361/235; 422/186.29
(58) Field of Classification Search .............. 96/2, 96/3, 19, 21–24, 68, 69, 80–82, 97, 99; 95/2–7, 95/81; 361/225–235; 422/186.04, 186.29
See application file for complete search history.

(56) References Cited

U.S. PATENT DOCUMENTS

| | | | | |
|---|---|---|---|---|
| 3,059,110 A | * | 10/1962 | Japolsky | .................... 250/291 |
| 4,090,855 A | * | 5/1978 | Hora et al. | ....................... 96/3 |
| 4,654,054 A | * | 3/1987 | Snaddon et al. | ................ 96/68 |
| 5,055,115 A | * | 10/1991 | Yikai et al. | .................... 96/59 |
| 5,077,500 A | | 12/1991 | Török et al. | |

(Continued)

FOREIGN PATENT DOCUMENTS

DE      3816245 A1  *  4/1989  ...................... 96/3

(Continued)

*Primary Examiner*—Richard L Chiesa
(74) *Attorney, Agent, or Firm*—Ogilvy Renault, LLP; Isabelle Chabot (57) ABSTRACT

A system for decontaminating a gas is provided. The system includes: a passageway containing at least one set of two or three electrodes. If the set contains three electrodes, it has two outer electrodes electrically connected together and one inner electrode. A high voltage waveform source for creating electrical fields between the electrodes, wherein the electrical fields interact with the gas to create an electronic current having a desired average energy level to at least match the energy level of the molecular bonds of the contaminants to be ruptured and wherein the set has either (a) at least one surface of the inner electrode and a corresponding exposed surface of the outer electrodes (in the case of a set with two electrodes, both exposed surfaces) are fitted with protuberances having a controlled geometry controlling an amplification factor of the electric field at extremities of the protuberances; or (b) a space between at least one outer electrode and the inner electrode (in the case of a set with two electrodes, a space between the electrodes) is at least partially filled with elements made for a dielectric material.

21 Claims, 8 Drawing Sheets

U.S. PATENT DOCUMENTS

| | | | |
|---|---|---|---|
| 5,248,324 A * | 9/1993 | Hara | 96/37 |
| 5,476,539 A * | 12/1995 | Suzuki et al. | 96/44 |
| 5,547,496 A * | 8/1996 | Hara | 96/79 |
| 5,733,360 A * | 3/1998 | Feldman et al. | 95/78 |
| 6,245,132 B1 | 6/2001 | Feldman et al. | |
| 6,375,714 B1 * | 4/2002 | Rump et al. | 95/3 |
| 6,504,308 B1 | 1/2003 | Krichtafovitch et al. | |
| 6,664,741 B1 | 12/2003 | Krichtafovitch | |
| 6,680,420 B2 * | 1/2004 | Pang et al. | 118/639 |
| 6,709,490 B1 * | 3/2004 | Calderon De Los Santos | 96/3 |
| 7,122,070 B1 * | 10/2006 | Krichtafovitch | 95/2 |
| 2007/0022876 A1 * | 2/2007 | Hess | 95/28 |

FOREIGN PATENT DOCUMENTS

| | | |
|---|---|---|
| EP | 0 600 101 | 6/1994 |
| EP | 1 194 175 B1 | 4/2003 |
| WO | WO0249767 | 6/2002 |

\* cited by examiner

FIG_4

FIG_5

SYSTEM FOR TREATING CONTAMINATED GAS

CROSS-REFERENCE TO RELATED APPLICATIONS

This application is the national stage of International Application No. PCT/CA05/00167, filed on Feb. 10, 2005.

This application claims priority of Canadian patent application No. 2,457,456 filed on Feb. 11, 2004 by Applicant, the specification of which is hereby incorporated by reference.

BACKGROUND OF THE INVENTION

1. Field of the Invention

The present invention relates to air and other gas decontamination process.

2. Description of Prior Art

Several patents (see for instance U.S. Pat. Nos. 6,245,132 and 6,664,741 and European patent No 1,194,175) have recognized the fact that ionization produced by a set of electrodes can capture contaminant material in a fluid such as air and destroy to some extent certain living biological contaminants. These patents are based on the use of corona electrodes to generate ions and electrically charge the contaminants and then capture the contaminants on an attracting electrode. Other ones are using interaction with a flux of electrons and various absorbing materials to destroy or to sterilize the contaminants. These patents describe different types of electrodes such as wires, needle point, razor blade to form the emitting electrode and flat or cylindrical attracting electrodes.

In particular, European patent No 1,194,175, granted on Sep. 9, 2003 and entitled <<Method for Treating a Gaseous Medium Containing Contaminating Particles>>, is describing a method in which the fluid to be treated is accelerated to form a swirling air vein and made to interact with a first electron flux and then to have the ionized particles interacting with a second electron flux to transform the contaminant into gas. The fluid is then passing through a porous material where chemical reactions occur and where the contaminated gas is transformed into non-toxic gas. The destruction of the contaminant is accomplished through the interaction of the fluid with an accelerated electron flux. The device incorporates some resonant magnetic cavities. No means to achieve such resonance are described. Furthermore no specific means to first extract from the electrodes and secondly to generate an electron flux having specific electrons energy levels are discussed and no means not to generate undesirable by-products such as ozone or NOx are addressed or claimed. The device is using a DC potential. No means to prevent arcing of the device are discussed.

U.S. Pat. No. 6,664,741, granted on Dec. 16, 2003 and entitled <<Method of and Apparatus for Electrostatic Fluid Acceleration Control of a Fluid Flow>>, recognized that in order to increase the ions generation at the electrode it is advantageous to increase significantly the electrode AC current component. To achieve this the patent is using electrodes with a significant capacitance feed by a DC switching power supply having a relatively large ripple voltage component producing the AC voltage excitation to the electrode capacitance. The AC current generated is being defined by the AC voltage of the ripple divided by the impedance of the electrode capacitance at the switching frequency. The AC current is thus proportional to that AC voltage and to the electrode capacitance at a specific switching frequency. One draw-back is that the electrodes require a relatively large capacitance to generate any significant current to improve the efficiency considering also that the power supply switching frequency is limited. Also the large AC voltage component superposed on the DC supply modulates to some extent the electron energies in the discharge.

U.S. Pat. No. 6,245,132, granted on Jun. 12, 2001 and entitled <<Air Filter with Combined Enhanced Collection Efficiency and Surface Sterilization>>, is using a basic filter that is sandwiched between two electrodes fed by a DC or AC or RF electrical source. The DC electrostatic field is used to attract the contaminant biological material, and intermittently a sterilization field using an AC or DC or RF source of enough intensity is applied to generate a surface plasma and thus destroying the contaminant biological material. No specific means for increasing the discharged current without increasing the electrical potential is described.

European patent No 0,600,101, granted on Jun. 8, 1994 and entitled <<Device for Biological Cleaning and Filtration of Air>>, is using corona discharging electrode and a non-discharging electrode to produce ions. The discharging electrode being a needle supplied with a large DC potential. Porous material is used in line of the airflow and an electrostatic precipitator is used to retain the contaminants. However, it does not provide an efficient current of particular electron energy level to destroy the contaminants or to control unwanted by-products.

International patent application WO 02/49767, published on Jun. 27, 2002 and entitled <<Electrostatic Device for Ionic Air Emission>> is suggesting a specific geometry of the receptive electrode, in a corona discharge system, to improve and make the collection of contaminants more homogeneous over the electrode surface thus improving its efficiency. It does not provide specific means to control the ions energy generation or the energy level.

U.S. Pat. No. 5,077,500, granted on Dec. 13, 1991 and entitled <<Air Transporting Arrangement>>, covers a specific geometry of the electrodes and the use of a dual power supply arrangement where one power supply controls the ions generation and the second one their acceleration. The system's description does not propose any resonant mechanism to generate the ions and does not address the control of any specific energy level to avoid generating undesirable by-products.

U.S. Pat. No. 6,504,308, granted on Jan. 7, 2003 and entitled <<Electrostatic Fluid Accelerator>>, covers some specific geometries of corona discharge accelerating and shielding electrodes to improve an electrostatic fluid accelerator. Although is it mentioned that it will not produce substantial undesired ozone and nitrogen oxides when the fluid is air, it is not described how this can be achieved. Reference is strictly made to a voltage setting within two extreme limits: "a voltage between the said corona electrodes and said exciting electrodes is maintained between the corona on set voltage and the breakdown voltage". With this technology, in order to generate a significant amount of ions, an extremely large electrical field must be generated at the tip of the corona electrodes. This very large electrical field produces high-energy particles that are susceptible to generate undesired by-products. A compromise is thus made between the quantity of ions generated and the production of undesired by-products.

SUMMARY OF THE INVENTION

It is an object of the present invention to provide a process for treating air that can contain airborne biological contaminants as well as non-living harmful contaminants that can be harmful if breathed by human and/or livestock animals and/or plants.

It is another object of the invention to provide a process for treating air in close storage space where the food or goods can be contaminated by the air or by the release of by-products from the stored food or goods, such as spores, decomposing products, maturating products, volatile organic compound etc. In such condition the released by-products by the food or goods can also contaminate the air.

This invention relates to a method of decontaminating, purifying and/or sterilizing air that contains undesired products such as airborne pathogenic agents or microorganisms such as spores, bacteria, viruses, yeasts and moulds. The method can also be used to decontaminate a gas which contains non-living substances such as volatile organic compounds (VOC), fumes, organophosphates, etc. The method consists in damaging and breaking up the contaminant molecular structure by oxidation, reduction and chemical bond rupture. Through this process the microorganisms or the contaminants are inactivated through structural damages to the cellular membrane and/or the nucleus membrane and/or to the DNA structure or by breaking the contaminant into simpler non-toxic molecular structures. This is accomplished by creating through the air to be treated, various electronic currents having a plurality of specific and controlled average kinetic energies matching or exceeding the desired chemical bonds to be affected and/or ruptured and/or oxidized in the contaminants. The air interaction with such various currents, under specific energies, sufficient intensities and exposition time is achieved by the use of sets of specially configured electrodes designed to produce and control the desired electronic kinetic energy and accomplished through several stages to decontaminate and/or sterilize the air or gas and to finally remove undesirable by-products that can be present so that it can be safely used directly or stored.

According to one broad aspect of the present invention, there is provided a multi-electrode system for decontaminating a gas containing contaminants flowing therein. The system comprises: a passageway for allowing the gas to flow from a first end to a second end of the passageway; at least one set of three electrodes having two outer electrodes electrically connected together forming a first terminal and one inner electrode placed between the two outer electrodes and forming a second terminal, wherein each set is placed within the passageway and in one of a perpendicular and a parallel orientation to the flow of gas and wherein the set is permeable to the gas flow when placed in a perpendicular orientation to the gas flow; a high voltage waveform source for supplying the first and second terminals and creating electrical fields between the outer electrodes and the inner electrode, wherein the electrical fields interacting with the gas to create an electronic current having a desired average energy level to at least match the energy level of the molecular bonds of the contaminants to be at least one of ruptured, and/or damaged and/or modified; and wherein the set has at least one of (a) at least one surface of the inner electrode and a corresponding exposed surface of the outer electrodes which are fitted with protuberances having a controlled geometry on the surface thereby controlling amplification factor of the electric field at extremities of the protuberances; and (b) a space between at least one outer electrode and the inner electrode which is at least partially filled with elements made from a dielectric material.

According to another broad aspect, there is provided a multi-electrode system for decontaminating a gas containing contaminants flowing therein. The system comprises: a passageway for allowing the gas to flow from a first end to a second end of the passageway; at least one set of two electrodes each having a terminal, wherein each set is placed within the passageway and in one of a perpendicular and a parallel orientation to the flow of gas and wherein the set is permeable to the gas flow when placed in a perpendicular orientation to the gas flow; a high voltage waveform source for supplying the terminals and creating an electrical field between the electrodes, wherein the electrical field interacts with the gas to create an electronic current having a desired average energy level to at least match the energy level of the molecular bonds of the contaminants to be at least one of ruptured, damaged and modified; and wherein the set has at least one of (a) an exposed surface of the electrodes is fitted with protuberances having a controlled geometry on the surface thereby controlling an amplification factor of the electric field at extremities of the protuberances; and (b) a space between the electrodes is at least partially filled with elements made from a dielectric material.

A system for decontaminating a gas is provided. The system comprises: a passageway containing at least one set of two or three electrodes. If the set contains three electrodes, it has two outer electrodes electrically connected together and one inner electrode. A high voltage waveform source for creating electrical fields between the electrodes, wherein the electrical fields interact with the gas to create an electronic current having a desired average energy level to at least match the energy level of the molecular bonds of the contaminants to be ruptured and wherein the set has either (a) at least one surface of the inner electrode and a corresponding exposed surface of the outer electrodes (in the case of a set with two electrodes, both exposed surfaces) are fitted with protuberances having a controlled geometry controlling an amplification factor of the electric field at extremities of the protuberances; or (b) a space between at least one outer electrode and the inner electrode (in the case of a set with two electrodes, a space between the electrodes) is at least partially filled with elements made from a dielectric material.

In the art, the term "sterilization" is used to mean the act of removing or inactivating (render non-living and non-self-replicating) all microorganisms from a medium, a typical acceptable level of contamination following a sterilization being 1 particle per $10^6$ or $10^7$. The term "decontamination" is used in the art to mean the removal or inactivating of most microorganisms from a medium, a typical acceptable level of contamination following a decontamination being 1 particle per $10^4$ or $10^5$. Therefore, in the present application, the term "decontamination" is intended to include a decontamination of the gas so effective that a sterilization occurs.

It will be readily understood that the concept of "air" is included in the meaning of the term "gas". Indeed, "air" is understood to mean a colorless, odorless, tasteless, gaseous mixture, mainly nitrogen (approximately 78 percent) and oxygen (approximately 21 percent) with lesser amounts of argon, carbon dioxide, hydrogen, neon, helium, and other gases while "gas" is understood to mean any substance in the gaseous state. Therefore, "air" being in a gaseous state, it is a gas. In the present application, the term "gas" is intended to include air, as well as any other gases. The terms "air" and "gas" are used interchangeably.

In the present application, the term "contaminant" is intended to include: airborne pathogenic agents, microorganisms, spores, bacteria, viruses, yeasts, moulds, smoke, organophosphates, undesirable chemical substances, volatile organic compounds (VOC), particles such as dust particles, etc.

BRIEF DESCRIPTION OF THE DRAWINGS

Further features and advantages of the present invention will become apparent from the following detailed description, taken in combination with the appended drawings, in which.

DESCRIPTION OF THE PREFERRED EMBODIMENT

Figure 1:
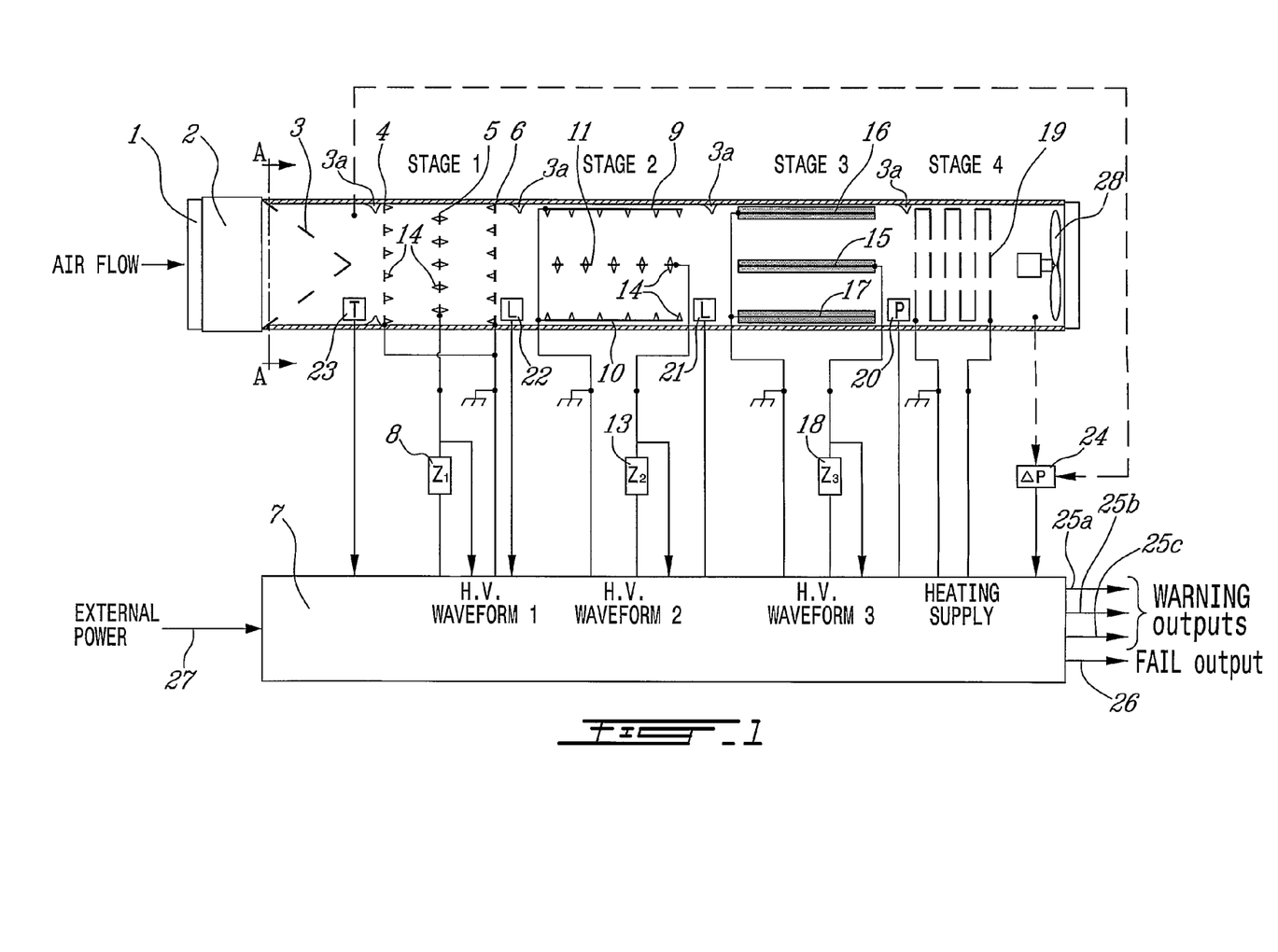
FIG. 1 is a schematical view of a system diagram in accordance with an embodiment of the present invention, including four basic processing stages.

Referring now to the drawings and, more particularly to FIG. 1, there is shown a system representation of an embodiment of the invention.

The air enters through an incoming duct adapter (1). A blower or a compressor (28) can be used to draw the air through the system and/or to compensate for the pressure drop across the system.

The air may be processed by a filter (2) to remove very large size particles present in the air such as fibers, dust, etc.

Figure 2:
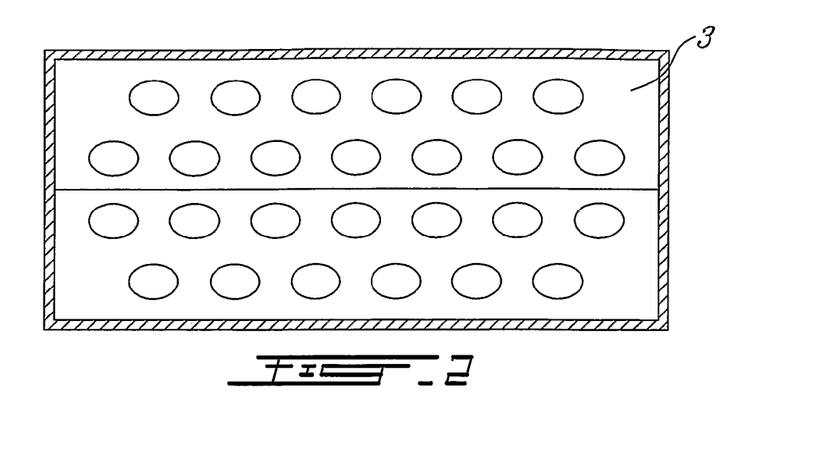
FIG. 2 is a schematical sectional view of the system diagram shown in FIG. 1 taken along line A-A and showing a detail of item 3.

The air then passes through a device (3) that makes the airflow slightly turbulent and provides a non-zero perpendicular speed with respect to the gas flow, such that the air will be fully exposed to the electronic current. The device (3) has a funnel shape perforated with holes of different diameters and shapes. Its geometry can be triangular, pyramidal or conical depending on the duct cross-section shape (see FIG. 2).

Other flow directors (3a) (shown partially for clarity), between the stages, ensure that the airflow is directed between the electrodes.

The air then passes through four basic stages of processing. The first two stages are used to break-up, structurally damage and oxidize the contaminants as such, the third stage collects the by-products and the fourth stage neutralizes the remaining undesirable by-products. The total number of stages can be increased by repeating one or more particular stages. The order of the stages and their distributed respective numbers can also be modified to achieve a desired specific processing.

Stage 1

This stage uses a basic set of three electrodes.

Figure 4:
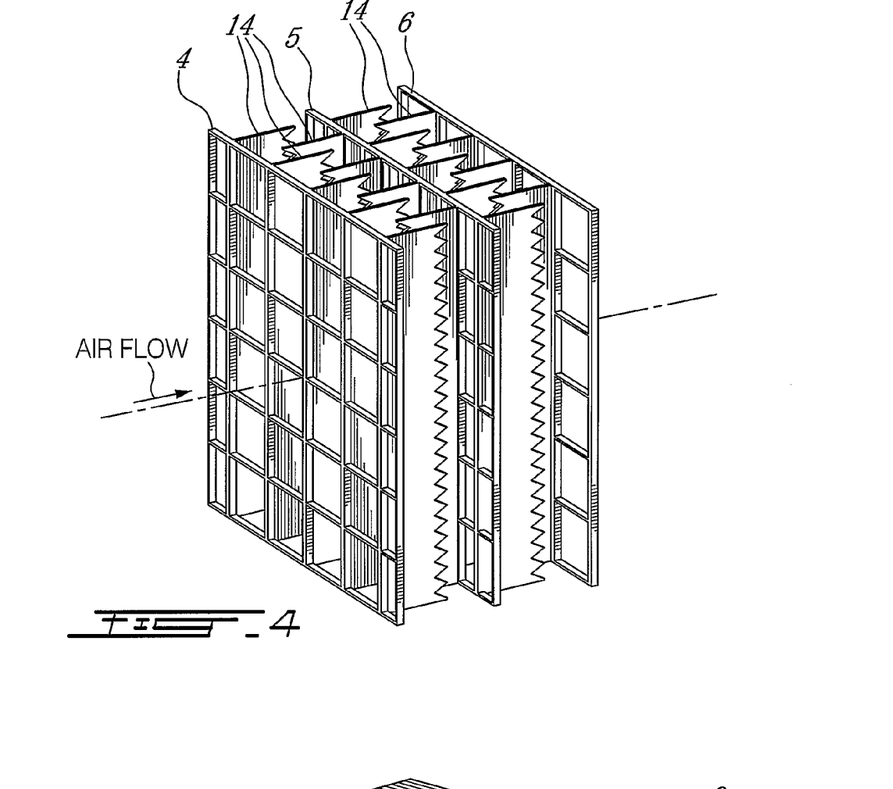
FIG. 4 is a schematical perspective view of the electrodes and peaks geometry used for stage 1 (1A) in accordance with an embodiment of the present invention.
Figure 5:
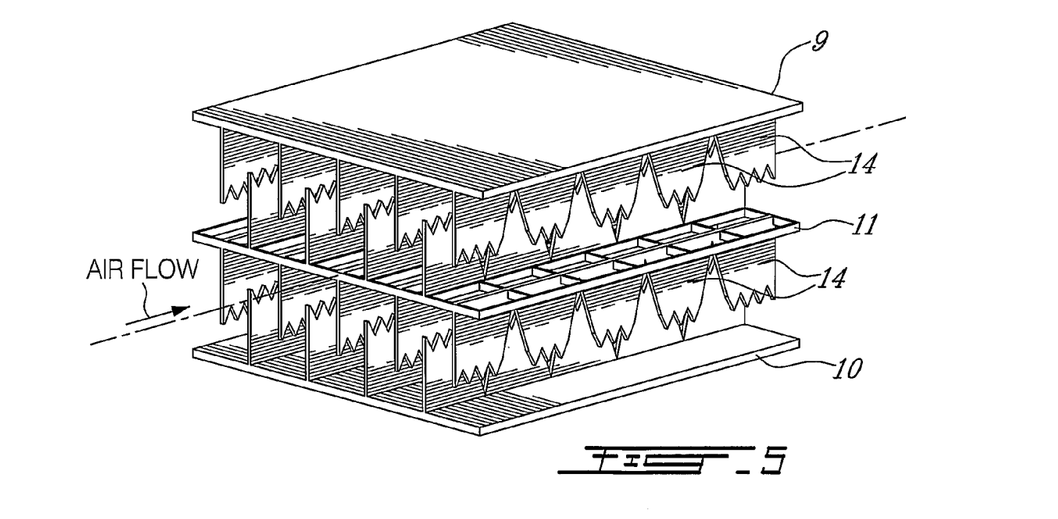
FIG. 5 is a schematical view of the electrodes and peaks geometry used for stage 2 in accordance with an embodiment of the present invention.

Two outer electrodes (4) and (6) are connected together and to one terminal of a high voltage waveform1 provided by a controller (7). An inner electrode (5) is connected through an impedance network Z1 (8) to another terminal of the corresponding high voltage waveform1 (7). The electrodes (4)-(5)-(6) are all made of conductive material and are transparent with regards to the airflow. The electrode surfaces are all placed perpendicular to the airflow. The electrodes (4)-(5)-(6) can also be referred to as being virtual electrodes in the sense that they are conductive and they define an electric field along the airflow over the whole cross-section surface but at the same time they do not restrict or block the airflow. The electrodes (4)-(5)-(6) can be made from wire grid or meshes, parallel wires or perforated sheet metal providing open spaces for the air to flow. The electrodes (4)-(5)-(6) are processed in such a way that the surfaces are not smooth but covered with peaks (14) that amplify the local electric field at their top edge and thus enhance the electron generation (extraction). The peaks (14) can take various shapes and are of, preferably but not limited to, triangular, square, rectangular or polygonal shapes. The exposed edges of the peaks (14) also have secondary peaks (not shown) along their exposed sides. The peak edges are made sharp with a specific tip geometry to produce a controlled electrical field amplification. The peaks (14) on each electrode (4)-(5)-(6) are arranged in such a way that each peak (14) is not facing directly another peak (14) on the opposite electrode (4)-(5)-(6). Preferably but not limited to the peaks (14) on one electrode (4)-(5)-(6), a collection of peak faces the opposite electrode (4)-(5)-(6) and this pattern is repeated alternatively between two electrodes (4)-(5)-(6). FIGS. 4 and 5 show embodiments for the peak arrangement. The inner electrode (5) and the outer electrodes (4)-(6) are forming an intrinsic electrical capacitance designated as Cstage1.

Stage 1A

Figure 3:
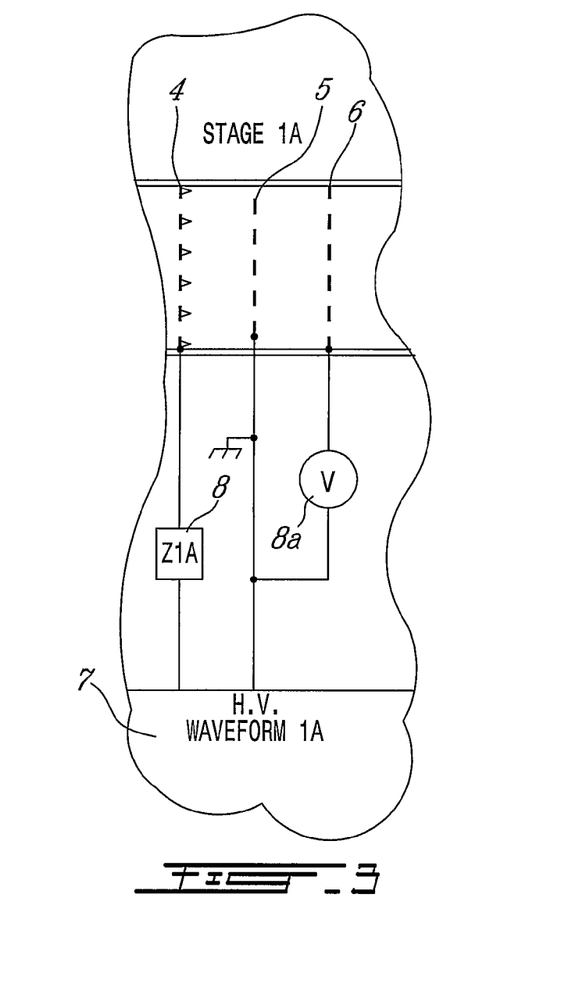
FIG. 3 is a schematical view of the electrode interconnections of stage 1A in accordance with an embodiment of the present invention.

Another embodiment of stage 1 is stage 1A shown in FIG. 3 that uses different electrode interconnections. The electrode (4) is connected to the impedance matching network Z1A (8) and electrode (5) to the other terminal of the high voltage waveform1A. The electrode (6) is connected to a large DC voltage supply (8a) and the other side of the DC supply is connected to the electrode (5). The waveform1A is restricted to negative polarity and the DC supply polarity is positive with respect to the electrode (6). Only electrode (4) has peaks (14) as described above in stage 1 but strictly limited to the space facing each other. The electrodes (5) and (6) have smooth surfaces and are virtual electrodes used strictly to accelerate the negative ions generated at electrode (4). Alternatively, the polarities of the voltage waveform1A and the DC supply can be inverted together. Under the stage 1A electrode configuration, the generated ions passing through the virtual electrode (5) are picked up and continue to be accelerated by the large DC field between the electrodes (5) and (6) until they become neutral. These ions through multiple collisions with neutral molecules and atoms impel a net force on the air mass within the electrodes. The net result is that these multiple directed collisions are effectively moving the air through the system from the left to the right with reference to FIG. 3. The stage 1A configuration enables the air to be processed without the need of a external air blower or circulator for a stand-alone application.

Stage 2

This stage uses a set of three electrodes.

The inner electrode (11) of stage 2 is similar to the inner electrode (5) described in stage 1 except that the electrode surfaces are placed parallel to the airflow and the peaks (14) have a limited orientation. The central electrode (11) is connected this time through an impedance network Z2 (13) to one terminal of high voltage waveform2 of the controller (7). Outer electrodes (9) and (10) are continuous (not virtual) and are also conductive and preferably reflective to light. The outer electrodes (9) and (10) are electrically connected together and connected to the other corresponding terminal of the high voltage waveform2 operating with a different set of parameters provided by the controller (7). The electrodes (9)-(10)-(11) are also processed in such a way that the surfaces are not smooth but covered with peaks (14) that amplify the local electric field at their tip edge and thus enhance the electron generation (extraction). The peaks (14) can take various shapes and are of, preferably but not limited to, triangular, square, rectangular or polygonal shapes. The exposed edges of the peaks (14) can also have secondary peaks (not shown) along their exposed sides. The peaks (14) on each electrode (9)-(10)-(11) are arranged in such a way that each peak (14) is not facing directly another peak (14) on the opposite electrode (9)-(10)-(11). Preferably, the peaks (14) on one electrode (9)-(10)-(11) are facing a collection of peaks (14) on the opposite electrode (9)-(10)-(11) and this pattern is repeated alternatively between two electrodes (9)-(10)-(11). The peak orientation is limited to peaks (14) that are aligned with the airflow such that they do not restrict the airflow significantly. The peak arrangement between the inner electrode (11) and the outer electrodes (9)-(10) are forming a staggered distribution. The inner and the two outer electrodes (9)-(10)-(11) are forming an intrinsic electrical capacitance designated as Cstage2. Note that in the drawings, the electrodes spacing has been exaggerated for better clarity.

This stage 2 is continuing the breakup of the contaminants using a different excitation voltage waveform that is more appropriate to deal now with smaller contaminant size. This section also provides ionization of the remaining broken-up contaminants to be handled by the third stage.

Preferably for stages land 2, the outer electrodes (4)-(6) and (9)-(10) respectively are referenced to earth ground for protection and electromagnetic shielding. The central electrodes (5)-(11) can alternatively be referenced to earth ground. In this later case, electrical insulation is required on the outer electrodes (4)-(6) and (9)-(10) for protection against shock hazard.

In general for stages 1 and 2, the outer electrodes (4)-(6)-(9)-(10) and the inner electrodes (5)-(11) are spaced by a distance d of the order of a fraction of a centimeter to a few centimeters with waveform amplitude applied to the electrodes of the order of a few Kilovolts. The intrinsic electrical field at the peaks determine the average kinetic energy of the free electrons. The specific energy of the free electrons generated is the key to control the breaking up process and the undesired by-products generation.

Resonant Electrode System

For stage 1, 1A and stage 2, in order to enhance the electronic current activity, a system that resonates the electrode AC current component is provided. (see FIG. 7A)

The electric current flowing between the inner and outers electrodes can be broken down to two components: the first one is the DC current component generated by the DC voltage component on the electrodes. That DC current is the corona discharge current of the order of few ten to few hundred microampere typically. The other component is the AC current component, which is due to the AC voltage component between the electrodes. That AC current is proportional to the electrode capacitance and the electrode AC voltage component.

Figure 6:
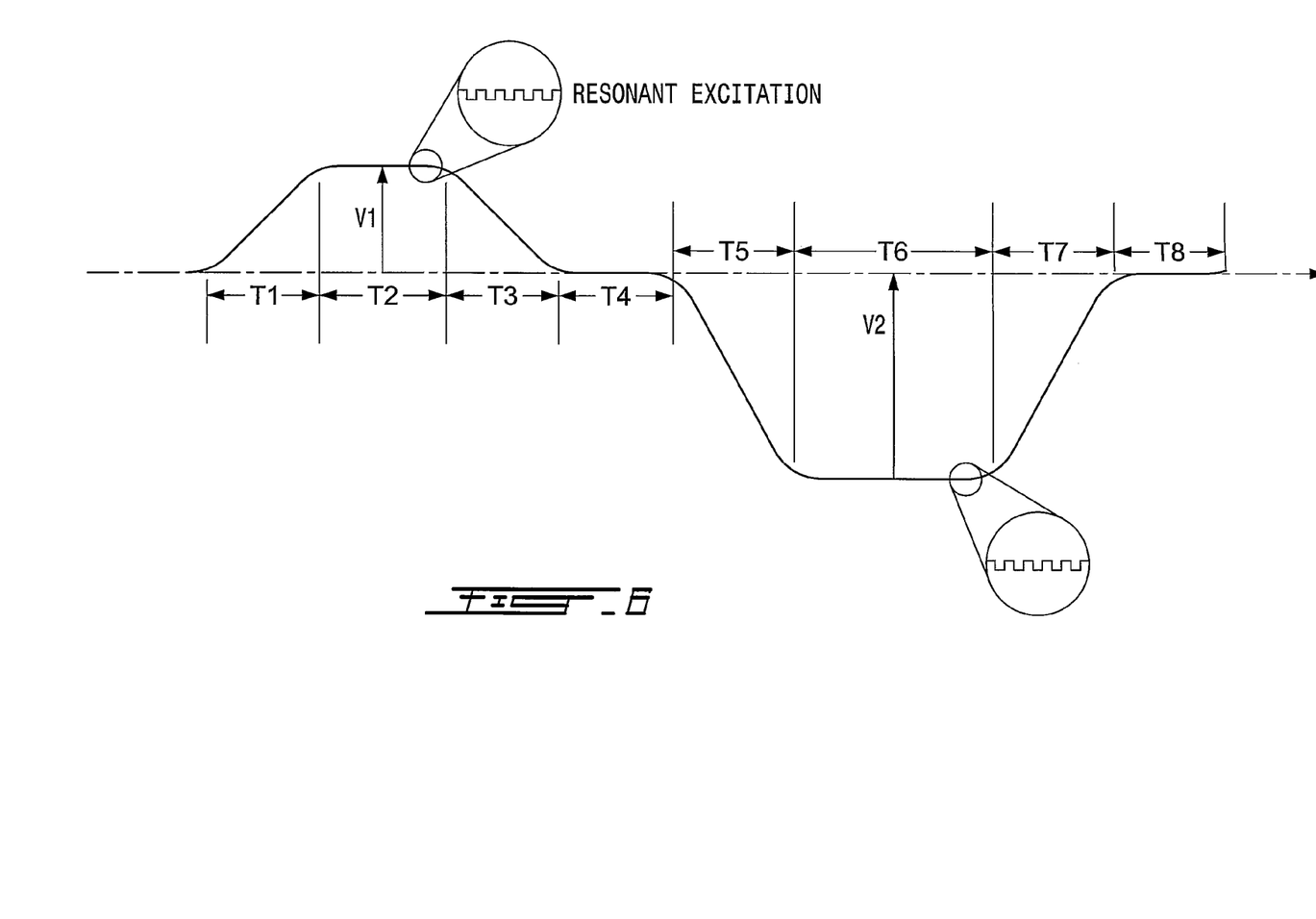
FIG. 6 a schematical view of a typical high voltage arbitrary waveform with the control parameters T1 to T8 for the duration and V1-V2 for the amplitude of the positive and negative cycle respectively in accordance with an embodiment of the present invention.
Figure 7A:
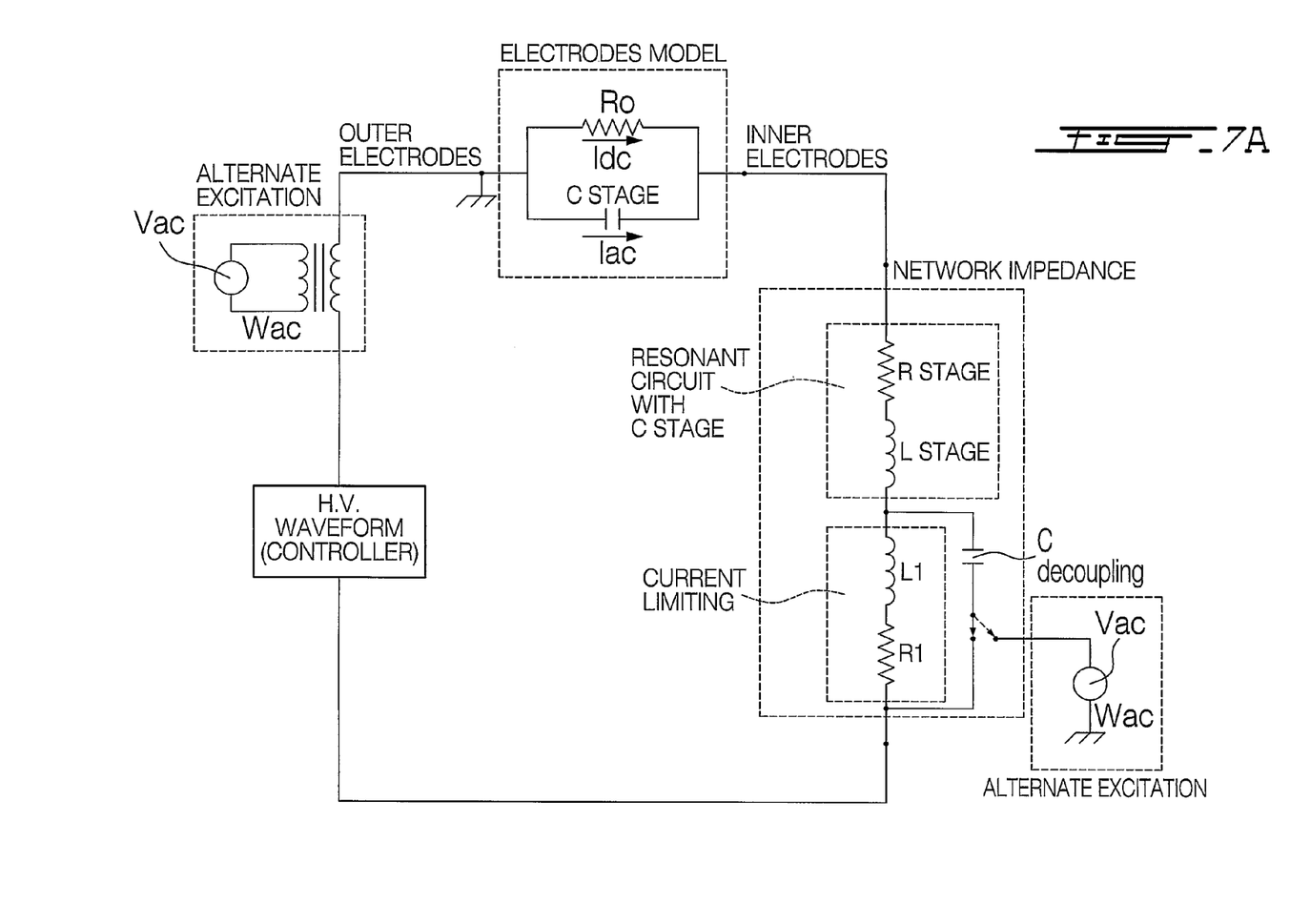
FIGS. 7a and 7b illustrate schematical views of the electrodes electrical model forming a resonant series circuit with the impedance network and the excitation supplied by the high voltage arbitrary waveform and alternate excitation means in accordance with an embodiment of the present invention, wherein the resonant circuit is respectively in series (FIG. 7a) and in parallel (FIG. 7b)

Using Ohm's law, one can write: Iac=Vac*Wac*Cstage where Iac is the current AC component in Ampere between the electrodes, Vac is the AC voltage component across the electrodes in Volt, Wac is the pulsating frequency of Vac in radian per second and Cstage is the capacitance in Farad of the electrodes. For a given specific stage, the capacitance is determined by the geometry of the electrodes and is of the order of a few to a few tens of pico-Farad. Previously known systems try to maximize the capacitance and the AC ripple voltage on the supply in order to increase the AC current since the ripple frequency is typically on the order of few ten kilohertz. However, this leads to high voltage ripple that will generate higher energy electrons and consequently, undesirable by-products will be formed. It is proposed to lower the effective impedance presented by Cstage of the electrodes by using, in series with the inner electrode and the voltage waveform, an inductive impedance Lstage that will series resonate with the electrodes capacitance at a higher frequency Wac=SQRT (1/Lstage*Cstage). Strictly speaking the resonant frequency is slightly shifted downward due to some resistive component part of the circuit. FIG. 7a provides a schematic representation of the embodiment. For the purpose of explaining the principle, it is considered that Wac as given above is a close approximation of the resonant frequency. At the resonant frequency Wac, the combined impedance of the electrode capacitance Cstage in series with the inductance Lstage becomes small such that the AC current increases even for a low excitation voltage (high Q factor of the resonant circuit). The excitation voltage at the resonant frequency Wac can be supplied by the high frequency component spectrum content of the relatively low frequency main high voltage waveform. Alternatively a high frequency very low voltage signal source having a frequency Wac can be superposed on the main high voltage waveform by using a small coupling capacitor or a transformer in series with the central electrode terminal (see FIG. 6). The electrode resonant circuit can also be coupled to a small amplifier feedback path to form an oscillator that uses the electrode resonant circuit as the tuning element. It is also important to note that the intrinsic current noise of the DC discharge itself that is very rich in high frequency components (wide band noise source) will excite the resonant circuit and will have a natural tendency to resonate the AC current component at a frequency around Wac.

Consequently the imaginary part of the network Z1(8) and Z2(13) shall be selected to be inductive around Wac with a value such that it will resonate in the megahertz area with the corresponding capacitance Cstage1 formed by the electrodes (4)-(5)-(6) and Cstage2 formed by the electrodes (9)-(10)-

Figure 7B:
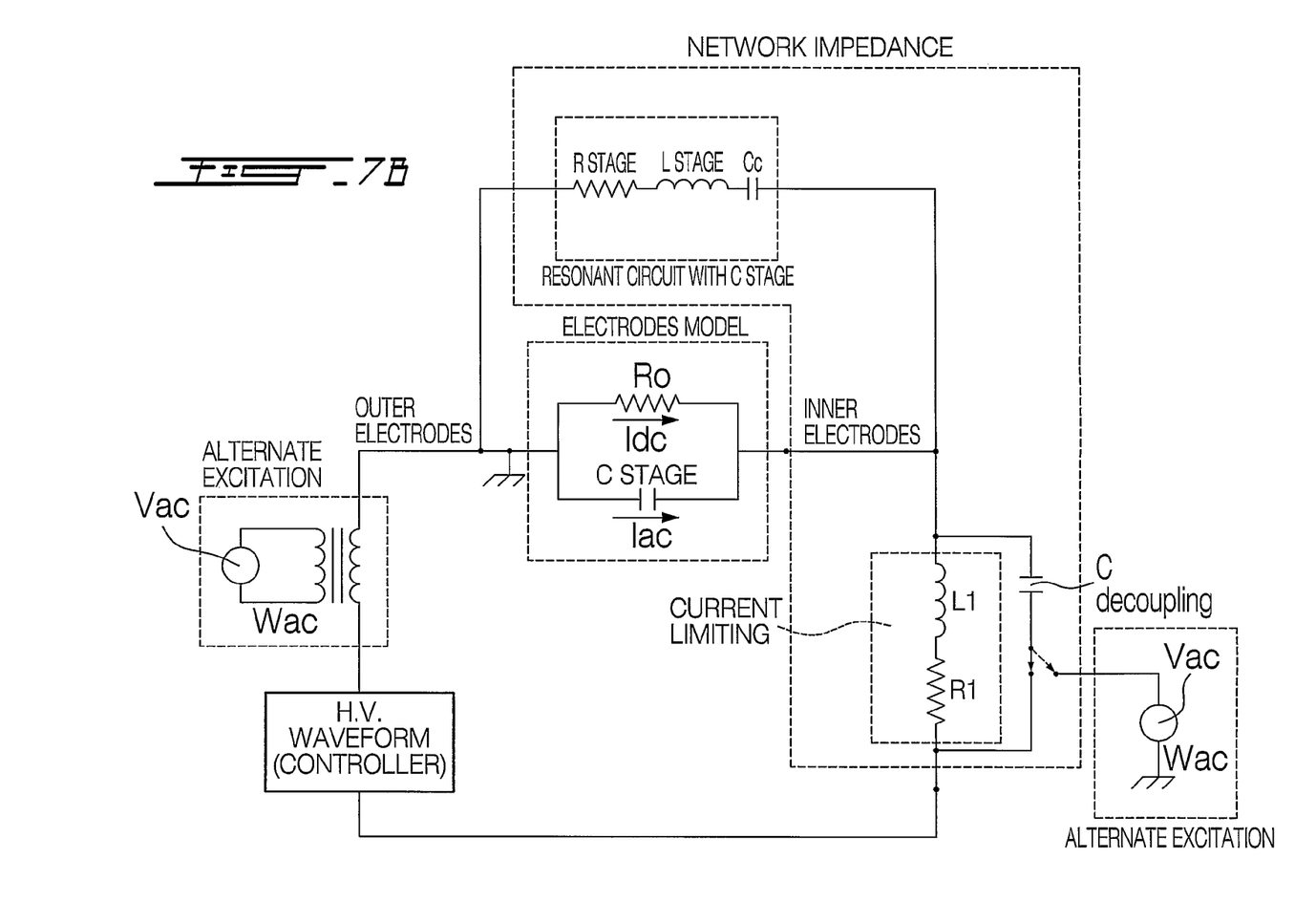

(11) at the desired frequencies Wac1 and Wac2 respectively. A small coupling or de-coupling capacitor, depending on the preferred implementation, of the order of ten times the Cstage capacitance, is used to close the resonant circuit. Alternatively the electrode capacitance can be resonated in parallel mode. FIG. 7b provides a schematic representation of this embodiment.

High Voltage Waveform

The controller (7) supplies different high voltage sources having their amplitudes and polarities that are controlled over time to make a specific voltage waveform for each particular air processing stage. The controller (7) is powered by an external power source (27). The voltage waveform is an arbitrary AC voltage waveform (see FIG. 6) having a specific amplitude repetition pattern with controlled, on-time periods (T2 and T6), off-time periods (T4 and T8), rise times (T1 and T5), fall times (T3 and T7) and possibly a DC offset voltage component (not shown). These controlled waveform parameters are very important for the following reasons:

The rise and fall times of the main voltage waveform are controlled to limit undesirable avalanche condition between the electrodes. The positive and negative voltage amplitudes are controlling the desirable mean energy level of the electrons. The polarity of the discharge voltage (V1 and V2) provides positive and negative coronas with their respective mean electron energy distribution. The on-time of the waveform, either positive or negative, controls the contaminants exposition time. The off-time provides a mean to extinguish possible arcing situation. The repetition rate can also be preferably selected based on the gas transit time between two stages having opposite polarities. This ensures that the contaminants are exposed over time to charge and discharge current cycles that are damaging their structures thus improving the system reactivity.

Stage 3

The outer electrodes (16) and (17) are connected together and to one terminal of a high voltage waveform3 provided by the controller (7). The inner or central electrode (15) is connected through an impedance network Z3 (18) to the other terminal of the corresponding high voltage waveform3 of the controller (7). The electrodes (15)-(16)-(17) composing stage 3 are conductive and free of any peak (14). These electrodes (15)-(16)-(17) are arranged in such a way that the electrical field generated between the electrodes (15)-(16)-(17) is not constant over the spacing distance but has a gradient. For example, one of many possible ways to achieve this field gradient is to make the effective surface of central electrode (15) significantly smaller than the surface of the outer electrodes (16)-(17). Another possible way, is to fill the space between the electrodes with dielectric material that is highly permeable with respect to the gas flow. The open spaces within the permeable dielectric and the points of contact or close proximity between two grains or cells of the permeable dielectric material produce locally a large electrical field amplification and gradient. The electrodes can be enclosed in a slightly leaky dielectric to dissipate the captured ion charges. The high voltage waveform3 has preferably a very high DC content. The impedance network Z3 (18) in this case provides a protection to limit the current feeding the electrodes (15)-(16)-(17) in case of a malfunction. The stage 3 can also be realized with virtual or permeable electrodes as described for stage 1, free of peaks, filled with permeable dielectric, and placed parallel or perpendicular to the gas flow.

The role of stage 3 is to capture the remaining contaminant particles and by-products that are present in the gas. The dielectric coating effectively increases the electric field within the electrode spacing. The charged contaminants as well as the neutral ones will be attracted and will attach themselves to the surface of the dielectric due to the strong electrical field and in the case of neutral contaminants due to their inherent electric dipole moment interacting with the electrical field gradient. The electrode surfaces and the dielectric volume between the electrodes 1 can be coated with a chemical substance (catalyst or others) that will react or reduce or neutralize the undesired by-products. This stage shall also be built in such a way that the electrodes (15)-(16)-(17) and the dielectric filler are easily accessible for cleaning or replacement.

Stage 4

Once the gas flowing through the stages gets fully processed over stages 1-2-3, the air penetrates into a fourth stage. This neutralizer stage is composed of a series of staggered wires or fine wire meshes (19), isolated from each other, that are electrically grounded (19) to earth, so that any remaining charged particles are neutralized. The wires or the meshes are coated with a catalytic material that produces the breakdown of ozone that can be present in small quantity after the first three stages especially during high electron energy exposure. To improve efficiency, the wires or the metal meshes can act as an heater to raise the temperature of the coating thus improving, if required, the catalytic conversion process. Stage 4 can be repeated with different catalyst materials.

Controller

The controller (7) generates the various voltage waveforms for the different stages. The controller (7) reads the air pressure (20) and temperature (23) in the unit volume to effectively establish the actual air density and controls, for each stage, the voltage waveforms WSn using a control law for example but not limited to:

$$WSn \text{applied} = (WSn0 \text{ at } P0 \text{ and } T0) \times ((P\text{actual} \times T0)/(T\text{actual} \times P0))^K.$$

Where WSn0 is the voltage waveform at P0 and T0 for stage n, P0 is the sea level reference pressure, T0 is the sea level reference temperature and where P0 and T0 determine the reference density, Pactual is the measured air operating pressure, Tactual is the measured air operating temperature, WSn is the applied voltage waveform to the electrodes corresponding to stage n and K is an exponent normally equal or close to one when the ratio of (Pactual×T0)/(Tactual×P0) is between 0.8 and 1.2. For a ratio outside that range, K takes other values.

The controller (7) interfaces with photo detectors (21) and (22) that are sensitive to the light radiation emitted by the plasma within the electrodes of stages 1 and 2. The level of the detected light is used to verify that the actual sterilization or decontamination is taking place and consequently that the sterilizer operates properly. If an un-proper level of light emitted by the plasma is detected, the controller (7) issues a warning (25) to the operators or the users.

The photo detectors (21) and (22) can be composed of a plurality of detectors/filters, each of these detectors/filters being sensitive to a different specific light wavelength band corresponding to a specific ionization or rupture energy of a chemical reaction.

The controller (7) reads each wavelength band intensity. The controller (7) then compensates for the different optical filter losses and detector sensitivities to produce a histogram of the photoemission spectrum of the plasma within the electrodes. The controller then imposes criteria on the intensity of each band to produce a valid signal meaning that the sterilizer is operational. The criteria can be simply, but not limited to, the presence of a minimum level of a particular band or a group of bands and/or the absence above a maximum level of another band or another group of band.

The controller (7) reads the differential air pressure (24) between the entry and the exit of the system. This pressure difference is related to the flow of air through the system and is used to provide operators/users feedback on the quantity of air processed. When a too low-pressure drop condition is detected between the entry and the exit of the system, a warning indication is provided that not enough airflow is circulating through the system If a too high-pressure drop is detected, it is an indication that the airflow capacity of the system is exceeded or that the system is clogged. In all the above cases, a warning (25) shall be issued to the operators or users.

The controller (7) reads the electrode currents for the various stages. These measurements enable the controller (7) to verify that the device is operating within proper preset parameters based on the operating voltage. This feature is used to issue a malfunction warning (25) to the operator in the case that an out of limits current is detected. The current readings may also be used to adjust the electrodes voltage. A too high current can be an indication that the system is dirty and that stray conduction paths can exist or that an arc can be actually taking place. A too low current can be an indication that the plasma is not forming within the electrodes and that the sterilization or decontamination is not taking place.

The high voltage supply at the electrodes for each stage can also be monitored to be within certain preset values in conjunction with the others parameters described above in order to determine the proper operation of the system, and issue a warning (25) to the operators or users in case of a malfunction. The voltage and the current readings can also be useful to diagnose a system failure.

The inner electrodes of the first three stages are feed by the corresponding voltage waveform using in series a current limiting device Z1-Z2-Z3 (8), (13) and (18). These impedance networks, beside providing an inductive component to resonate stage 1 (and 1A) and stage 2, are also used to prevent possible arc formation between the central and the outer electrodes. During an arc, the electric current would increase drastically and the limiter device would drop the electrode voltage thus preventing the arc to continue. Current limiting devices can be passive such as a resistor or an inductor or can be active electronic circuit or a combination of both. The current limiting function is part of the impedance network, which is also used to resonate the RF excitation current for stages 1-2. FIG. 7a present one possible arrangement of the network impedance that combines the Cstage1 or Cstage2 capacitance resonance function and the current limiting function to prevent arc formation.

Figure 8:
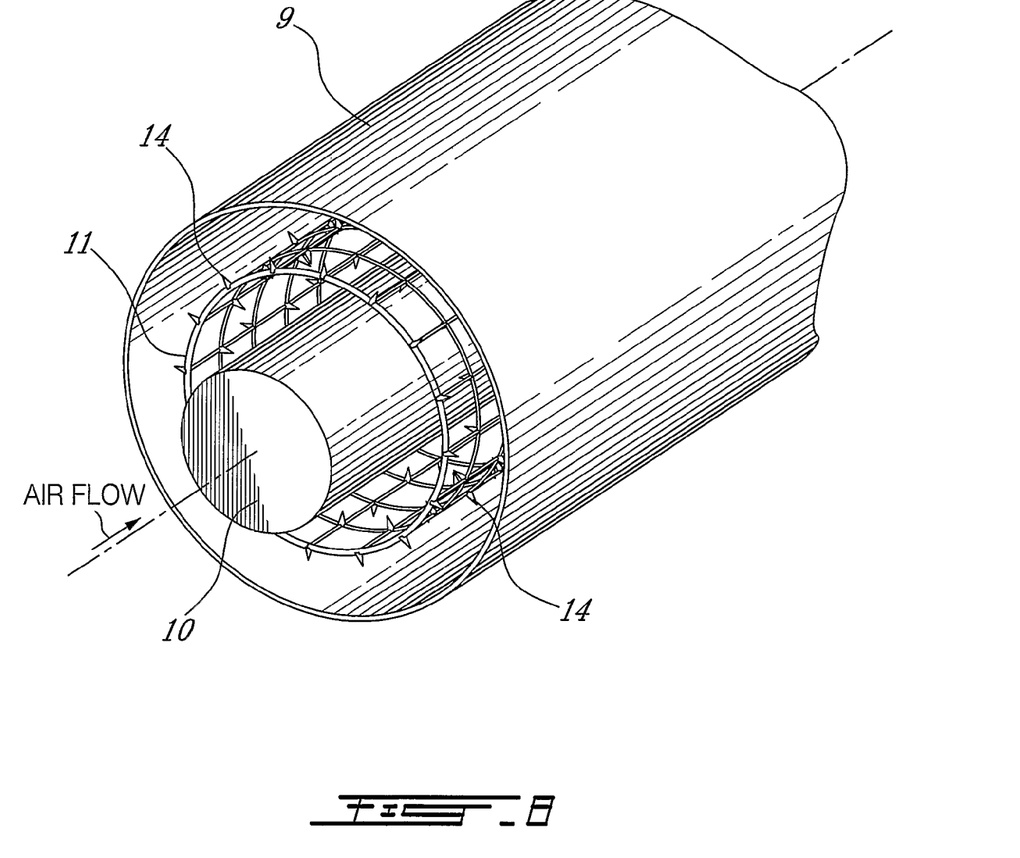
FIG. 8 is a schematical view of the electrodes using a cylindrical geometry for stage 2 in accordance with an embodiment of the present invention, wherein the peaks on the outer electrodes are not shown.

The basic planar geometry for stage 2 (FIG. 5) can also be modified to form a cylindrical electrode geometry (see FIG. 8).

Figure 9:
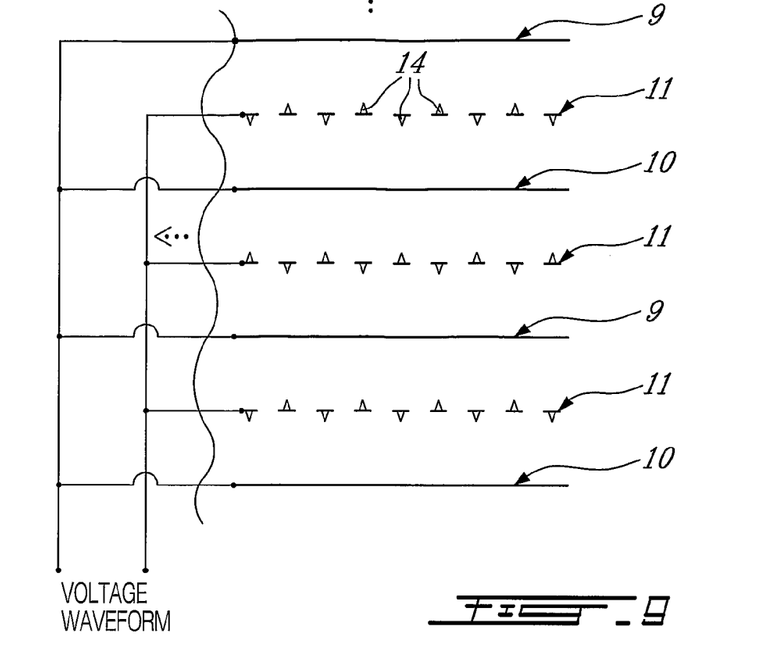
FIG. 9 is a schematical view of the stacking of multiple electrodes using planar geometry to increase the device capacity in accordance with an embodiment of the present invention, wherein the peaks on the outer electrodes are not shown.
Figure 10:
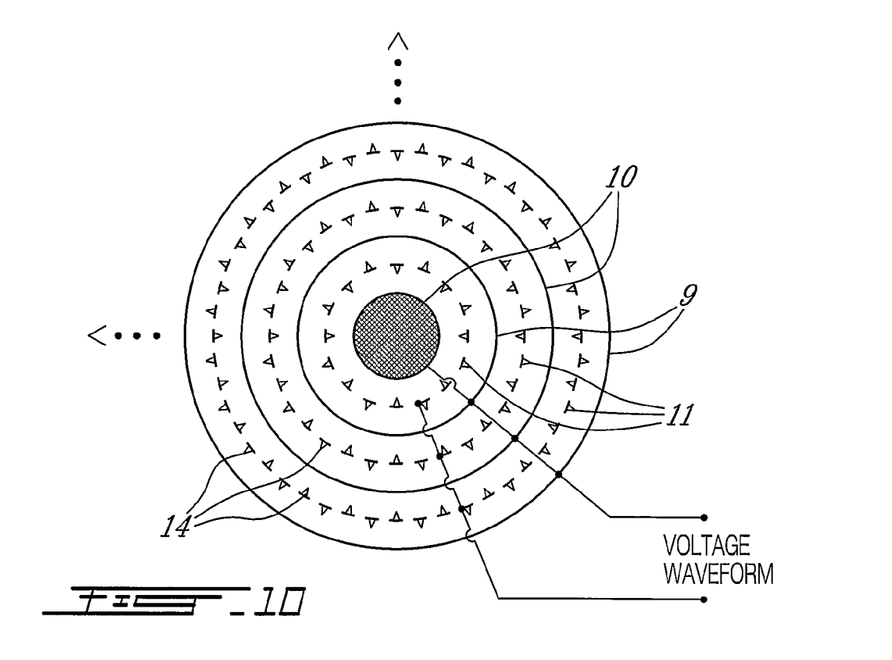
FIG. 10 is a schematical view of the stacking of multiple electrodes using cylindrical geometry to increase the device capacity in accordance with an embodiment of the present invention, wherein the peaks on the outer electrodes are not shown.

To improve the device capacity to process large air flows, the electrode geometry can be repeated to form a stack of electrodes. This increases the front section of the system and maintains the exposition time of the contaminants. This stacking of electrodes is applicable to the planar geometry (see FIG. 9) and to the cylindrical geometry (see FIG. 10).

As described hereinabove, the process of the present invention is applicable to treat air in buildings, shelters and transportation means such as trains, buses, aircrafts, spacecrafts, submarines, boats and cars by processing the air circulating into their respective ventilation systems. By adding a means such as a ventilator to circulate the air through the system, the system can be used as stand-alone in an enclosure where the air needs to be treated. The process can also be used to treat gases that are needed to be stored in pressurized reservoirs such as medical gas bottles and autonomous respiratory equipment for scuba diving, fire fighting, etc. The process is also applicable in the field of biological contamination protective suits and military gears where the existing filter on suit or mask can be replaced by or used in conjunction with the present invention.

The process also includes various means of monitoring that the device is effectively processing the air. This monitoring enables the operators or users to be warned in case of one or more malfunctions are detected. Since the device can be used in critical applications such as sterilizing or decontaminating hospital rooms, sterilizing or decontaminating the outside air used by military personnel in shelters or vehicles, and the like, the operation of monitoring of the system and the warning issues generated by the system are an integral part of the system and are important functions.

The process is also self adaptable to gas pressure and temperature (density) variation conditions encountered in, but not limited to, aircraft cabin pressurization, decompression chambers, etc.

As for the above-described embodiment, the air is processed in four basic stages where the first two stages are used to break-up the contaminants as such, the third stage collects the by-products and the fourth stage neutralizes the remaining undesirable by-products.

For stages one and two, a set of electrodes (2 or more) with a particular geometry, fed by a high voltage arbitrary voltage waveform, is used to create an electronic current density through the air. The electrodes are made to form an electrically resonant circuit that increases the AC current. FIG. 1 shows the system using a 3 electrodes set.

The system uses positive and negative voltage waveform (see FIG. 6), alternating or not over time, each current discharge being formed by a specific voltage polarity (V1 and V2) and amplitude duration (T2 and T6) to control the exposition time on the contaminants. The polarity of the voltage excitation on the electrodes determines the type of corona discharge current that is generated at the tips of the electrodes.

The specific geometry at the electrode tip amplifies locally the electrical field such that the discharge can be sustained. By controlling the voltage between the electrodes and the electrode tip geometry (amplification factor), the electrical field at the electrode tips is well controlled. The established electrical field at the tips is used to control the effective electrons energy distribution.

The physics of positive and negative corona currents are very different. At room temperature and pressure the electrons have the ability to undergo a significant degree of ionizing non elastic collisions. The mechanisms involved in both positive and negative corona current discharges rely on the strong electrical field at the tip of the electrode, so that once a neutral molecule is ionized (by a natural occurrence), the electron and the ion are accelerated in opposite direction and this prevents their recombination while imparting them with kinetic energy.

For the positive discharge cycle, the electrons are concentrated close to the tip surface of the electrode where a large electrical field exists. This inner region is the plasma region. There are much fewer free electrons in a positive discharge except close to the tips when compared with a negative discharge. The electrons in a positive discharge have a large kinetic energy and thus are more suited for high activation energy reactions. The flow of positive ions toward the receptive electrode possesses a low kinetic energy and this forms the outer or unipolar region. All the secondary electrons are generated by photon ionization.

For the negative discharge cycle, the electrons are allowed to drift out of the ionizing region of the electrode tips such that the plasma continues some distance from the tips. The total number of electrons is much greater than in the positive corona except that the electrons have predominantly a much lower kinetic energy when compared with the positive corona. For negative corona the dominant process to generate secondary electrons is the photoelectric process that is taking place at the electrode tip surface itself.

The stability of the negative current discharge is sustained with electronegative molecules present in the air such as oxygen and water vapor that capture easily free electrons in the outer region of the discharge and prevent the electrons from creating a narrow current channel developing into a spark. The negative discharge thus generates lower electron energies when compared to the positive discharge and is suitable for low activation energy reactions.

For both polarities of corona discharge it has been established that the electrical field is not modified significantly by the presence of the discharge due to the relatively low-density space charge distribution. The electron energy distribution can be approximated to a Maxwell one although the high end energy population is slightly lower. In such an approximation, the distribution mean energy becomes almost a linear function of the electrical field strength over the range of 3E6 to 30E6 Volt per meter and having a small downward departure from a straight line at the low end of the field.

Under these conditions and discharge mechanisms, through the electrical field (Et) intensity and polarity present at the electrode tip, the electrons acquire a controlled average kinetic energy so that when they interact with a molecular structure they break-up or rupture preferably specific chemical energy bonds.

The present invention uses these key processes to achieve the destruction of the contaminant.

The overall interaction with the air produces ionized molecules and atoms, excited molecules and atoms, free specific mean kinetic energy electrons, photons, chemical by-products, oxidation species, chemical bond ruptures and charge recombination in the contaminant. The net result is that the large molecular structures are broken down into several smaller segments and the pathogen contaminants are inactivated.

The three electrodes structure has another distinct advantage for stage 1 and 2. Since the inner electrode is virtual, i.e. highly transparent with respect to the air flow but having an electrical field of opposed direction on each of its sides, this create an ions trap and thus increases their exposition time to the photons and electrons instead of being neutralized right away at the electrode surface. For positive polarity of the inner electrode the negative ions are trapped. For negative polarity the positive ions are trapped.

Energetic photons are also generated in stages 1 and 2 when the exited molecules return to their basic states. In stage 2 these photons are reflected back and forth between the reflective outer electrodes due to fact that the central electrode is highly transparent (mesh, largely perforated sheet metal or wires). This feature increases the chance that these photons will ionize more material and will create, by photon energy absorption, damages and structural breakup of the contaminant.

The embodiments of the invention described above are intended to be exemplary only. The scope of the invention is therefore intended to be limited solely by the scope of the appended claims.

What is claimed is:

1. A multi-electrode system for decontaminating a gas containing contaminants flowing therein, comprising:
    a passageway for allowing said gas to flow from a first end to a second end of said passageway;
    at least one set of three electrodes having two outer electrodes electrically connected together forming a first terminal and one inner electrode placed between the two outer electrodes and forming a second terminal, wherein each set is placed within said passageway and in one of a perpendicular and a parallel orientation to said flow of gas and wherein said set is permeable to said gas flow when placed in a perpendicular orientation to the gas flow;
    a high voltage waveform source for supplying said first and second terminals and creating electrical fields between the outer electrodes and the inner electrode, wherein said electrical fields interact with the gas to create an electronic current having a desired average energy level to at least match the energy level of the molecular bonds of the contaminants to be at least one of ruptured, damaged and modified; and
    wherein said set has at least one of
        (a) at least one surface of said inner electrode and a corresponding exposed surface of said outer electrodes are fitted with protuberances having a controlled geometry on said surface thereby controlling amplification factor of said electric field at extremities of said protuberances; and
        (b) a space between at least one outer electrode and said inner electrode is at least partially filled with elements made from a dielectric material.

2. A multi-electrode system as claimed in claim 1, wherein said element made from a dielectric material is at least one of granular particles and fibers.

3. A multi-electrode system as claimed in claim 1, wherein said inner electrode has openings and ion traps are created within said openings due to the opposite electrical field direction on each side of said inner electrode.

4. A multi-electrode system as claimed in claim 1, wherein said energy level is greater than the energy level of the molecular bonds of the contaminants.

5. A multi-electrode system as claimed in claim 1, wherein an effective electric field at a tip of said protuberances is in the range of $10^6$V/m to $30*10^6$V/m.

6. A multi-electrode system as claimed in claim 1, wherein said protuberances are at least one of spikes, peaks and bumps.

7. A multi-electrode system as claimed in claim 1, wherein said contaminants are at least one of airborne pathogenic agents, microorganisms and undesirable chemical substances.

8. A multi-electrode system as claimed in claim 1, wherein each of said sets further comprises at least one added set of two electrodes, one inner and one outer and wherein all the inner electrodes are electrically connected together and all the outer electrodes are electrically connected together thereby forming together a capacitance set with two terminals having 1+N inner electrodes and 2+N outer electrodes where N is the number of added sets of two electrodes, and wherein N is an integer value greater than or equal to zero.

9. A multi-electrode system as claimed in claim 8,
    wherein said capacitance set resonates at an RF frequency with an impedance network in series to provide an RF electrical field between the electrodes superposed over the electric field provided by the high voltage waveform source;

wherein at least one terminal is connected in series with an impedance network;

wherein said impedance network has a first inductor and a first resistor in series connected to said terminal to provide a resonant electrode function;

wherein said impedance network has a second inductor and second resistor in series providing a current limiting function and connected in series with said first resistor and first inductor;

whereby each electrode set is forming a capacitive load impedance and wherein that load impedance is being resonated at radio frequency with the first inductor in series with the first resistor to increase the alternative current and improve the energy transfer between the high voltage waveform source and the electrode set.

10. A multi-electrode system as claimed in claim 8, wherein a plurality of said sets are provided and wherein each set of electrodes constitutes a decontamination stage and wherein said electrode sets are placed in succession in the gas flow and wherein each said stage has a specific electronic current density and average energy through its connection to a high voltage waveform source and creates between the electrodes a specific and controlled electrical field giving emitted electrons a controlled average specific energy susceptible to at least one of break-up and ionization of the specific chemical bonds in the contaminants which have an energy matching the specific average electron energy.

11. A multi-electrode system as claimed in claim 10, wherein each specific high voltage waveform (V1) from said high voltage waveform source is automatically adjusted to the ratio function of the measured air density (D1) to the reference air density (D0) corresponding to the reference voltage waveform (V0), by using the gas absolute temperature and pressure measurements to determine the gas density and using the formula: $V1=V0*(D1/D0)^k$ where k is selected in the range of 0.5 to 1.5.

12. A multi-electrode system as claimed in claim 1 wherein the two outer electrodes are formed integrally and create a decontamination stage formed with two electrodes.

13. A multi-electrode system as claimed in claim 1 wherein the sets of electrodes have a planar or cylindrical geometry.

14. A multi-electrode system as claimed in claim 2, wherein said particle is one of spherical, semi-spherical, ovoid and polygonal particle and wherein a diameter of said elements is between $1/10$ to $1/500$ of said space.

15. A multi-electrode system as claimed in claim 1, further comprising a controller which controls parameters of the electric field created by the high voltage waveform source.

16. A multi-electrode system as claimed in claim 15, further comprising sensors for operating conditions of said system and wherein said controller adjusts said parameters to control said high voltage waveform source.

17. A multi-electrode system as claimed in claim 16, wherein said sensors are at least one of a pressure sensor, a temperature sensor, a current sensor, a voltage sensor and a light sensor.

18. A multi-electrode system as claimed in claim 16, wherein said controller has a status detector for detecting an operation status of said system and issuing a warning if at least one of abnormal and malfunction status is detected.

19. A multi-electrode system as claimed in claim 1, further comprising
an additional set of three conductive electrodes having two outer electrodes electrically connected together forming a first terminal and one inner electrode placed between the two outer electrodes and forming a second terminal, wherein said set is placed within said passageway after said at least one set, in one of perpendicular and parallel orientation to said flow of gas and wherein said set is permeable to said gas flow when placed in a perpendicular orientation to the gas flow, said electrodes being conductive and free of any peak and being arranged such that the electrical field generated between the electrodes is not constant over the spacing distance and has a gradient;

said high voltage waveform source supplying said first and second terminals and creating an electrical fields between the outer electrodes and the inner electrode;

whereby said additional set captures remaining contaminants and contaminants by-products present in the gas.

20. A multi-electrode system as claimed in claim 1, further comprising:
a neutralizer stage composed of a series of one of staggered wires and fine wire meshes, isolated from each other, electrically grounded to earth at one end, placed within said passageway after said at least one set;

wherein said wires and said meshes are coated with a catalytic material;

wherein said wires and said meshes are connected to one of a voltage and a current source to heat and raise the temperature of the catalytic material;

wherein remaining charged particles and undesired byproducts in said gas are neutralized.

21. A multi-electrode system for decontaminating a gas containing contaminants flowing therein, comprising:
a passageway for allowing said gas to flow from a first end to a second end of said passageway;

at least one set of two electrodes each having a terminal, wherein each set is placed within said passageway and in one of a perpendicular and a parallel orientation to said flow of gas and wherein said set is permeable to said gas flow when placed in a perpendicular orientation to the gas flow;

a high voltage waveform source for supplying said terminals and creating an electrical field between the electrodes, wherein said electrical field interacts with the gas to create an electronic current having a desired average energy level to at least match the energy level of the molecular bonds of the contaminants to be at least one of ruptured, damaged and modified; and wherein said set has at least one of
(a) an exposed surface of said electrodes is fitted with protuberances having a controlled geometry on said surface thereby controlling an amplification factor of said electric field at extremities of said protuberances; and
(b) a space between said electrodes is at least partially filled with elements made from a dielectric material.

* * * * *